(12) United States Patent
Acharyulu et al.

(10) Patent No.: US 7,531,673 B2
(45) Date of Patent: May 12, 2009

(54) PREPARATION OF AMINO ACID AMIDES

(75) Inventors: Palle V. R. Acharyulu, Hyderabad (IN); C. M. Haricharan Raju, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 211 days.

(21) Appl. No.: 11/058,835

(22) Filed: Feb. 16, 2005

(65) Prior Publication Data

US 2005/0182262 A1   Aug. 18, 2005

Related U.S. Application Data

(60) Provisional application No. 60/545,428, filed on Feb. 18, 2004.

(51) Int. Cl.
*C07D 207/00* (2006.01)
(52) U.S. Cl. ...................................... 548/543; 548/550
(58) Field of Classification Search ................. 548/543, 548/550
See application file for complete search history.

(56) References Cited

U.S. PATENT DOCUMENTS 7,132,552 B2 * 11/2006 Dolitzky et al. ............. 548/543

* cited by examiner

*Primary Examiner*—Rei-tsang Shiao
(74) *Attorney, Agent, or Firm*—Robert A. Franks; Lee Banks; Anjum Swaroop

(57) ABSTRACT

A process for making amino acid amides, comprising reacting an amino acid, or acid salt of an amino acid, with a halogenating agent, or with a substance that reacts with carboxylic acids to form a leaving group, to form an intermediate, then reacting the intermediate with ammonia. When the amino acid or acid salt is enantiomerically pure, the amide will be a stereoisomer. An amide made by the process can be used to form levetiracetam.

5 Claims, 1 Drawing Sheet

PREPARATION OF AMINO ACID AMIDES

CROSS-REFERENCE TO RELATED APPLICATION

This application claims the benefit of U.S. Provisional Application 60/545,428 filed on Feb. 18, 2004, the entire disclosure of which is hereby incorporated by reference.

INTRODUCTION TO THE INVENTION

The present invention relates in one aspect to a process for preparing amino acid amides, a representative of which is useful as an intermediate for preparing the drug compound levetiracetam.

Levetiracetam is a drug that is useful for treating disorders of the nervous system, such as epilepsy, and has the chemical name (−)-(S)-α-ethyl-2-oxo-1-pyrrolidine acetamide, the formula $C_8H_{14}N_2O_2$, and the molecular weight 170.21. The current pharmaceutical products containing this drug are sold by UCB Pharma using the tradename KEPPRA, in the forms of tablets and a flavored liquid.

A preparation of levetiracetam is described in examples of U.S. Pat. Nos. 4,696,943, 4,837,223 and 4,943,639 to Gobert et al. These examples all begin with racemic α-ethyl-2-oxo-1-pyrrolidine acetamide that was described in British Patent No. 1,309,692 as 2-(2-oxo-pyrrolidino)-butyramide; this patent provides methods for preparing several related compounds.

There is a need for an improved process to prepare amino acid amide compounds, particularly processes that directly synthesize desired stereoisomers of the compounds.

SUMMARY OF THE INVENTION

The invention includes a process for making amino acid amides, comprising reacting an amino acid, or acid salt of an amino acid, with a halogenating agent, or with a substance that reacts with carboxylic acids to form a leaving group, to form an intermediate, then reacting the intermediate with ammonia. When the amino acid or acid salt is enantiomerically pure, the amide will be a stereoisomer.

In one aspect, the invention provides a process for preparing a stereoisomer of an amino acid amide having the structure:

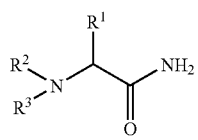

wherein $R^1$ is a normal or branched alkyl group having 1 to 10 carbon atoms, and $R^2$ and $R^3$ independently are hydrogen or a substituted or unsubstituted normal or branched alkyl group having 1 to 6 carbon atoms, or $R^1$ and $R^2$, or $R^2$ and $R^3$, and the nitrogen atom are members of a heterocyclic group having three to seven carbon atoms, the individual carbon atoms of the heterocyclic group independently being substituted or unsubstituted, comprising reacting an amino acid having the structure:

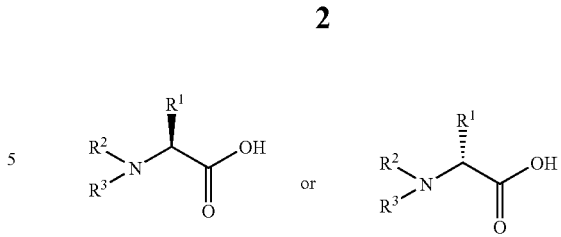

wherein $R^1$, $R^2$, and $R^3$ are as described above, or an acid salt of the amino acid, with a halogenating agent or with a substance that reacts with carboxylic acids to form a leaving group to form an intermediate, and subsequently reacting the intermediate with ammonia.

In another aspect, the invention provides a process for preparing (−)-(S)-α-ethyl-2-oxo-1-pyrrolidineacetamide, comprising reacting (S)-2-aminobutyramide hydrochloride with a compound having the structure:

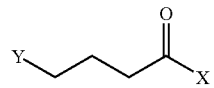

wherein X is Cl, Br, I, or another carboxylic acid activating group and Y is Cl, Br, I, mesyl, tosyl, and the like.

In a further aspect, the invention provides a process for preparing (−)-(S)-α-ethyl-2-oxo-1-pyrrolidineacetamide, comprising reacting (S)-2-aminobutyric acid hydrochloride with thionyl chloride to form an intermediate, reacting the intermediate with ammonia to form (S)-2-aminobutyramide hydrochloride, and reacting the (S)-2-aminobutyramide hydrochloride with 4-chlorobutyryl chloride.

DETAILED DESCRIPTION

Figure 1:
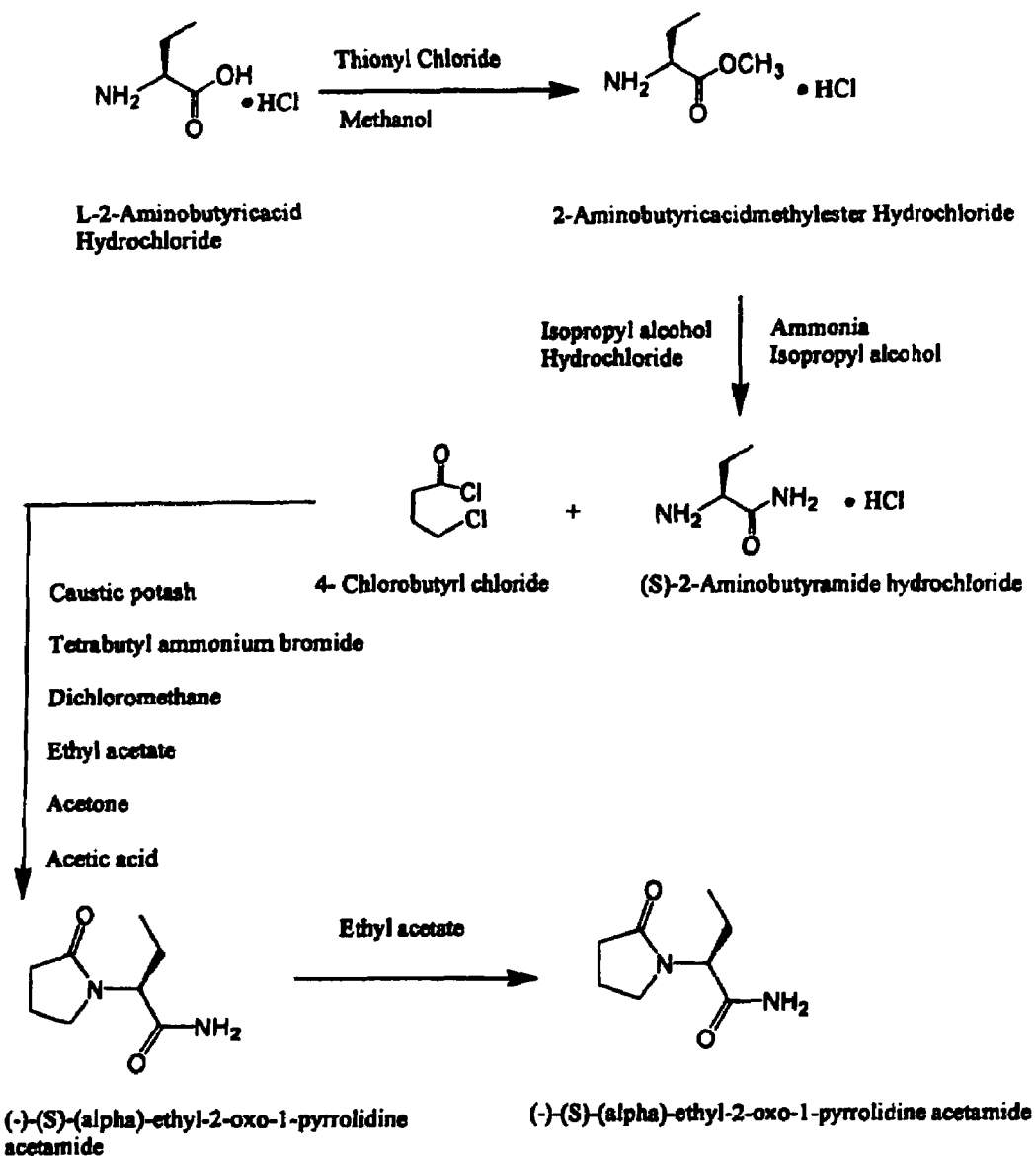
FIG. 1 is a schematic representation of a process for preparing levetiracetam.

The present invention includes a process for preparing amino acid amides, or amides of acid salts of amino acids, comprising reacting an amino acid or acid salt with a halogenating agent, or with a substance that reacts with carboxylic acids to form a leaving group, to form an intermediate, then reacting the intermediate with ammonia. When the amino acid or amino acid salt is enantiomerically pure, the amide is a stereoisomer.

In one aspect, the invention includes a process for preparing amino acid amides having the structure:

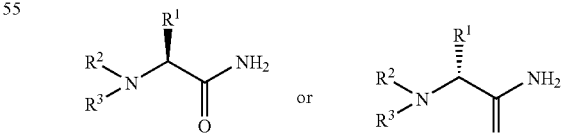

where: $R^1$ represents a normal or branched alkyl group having 1 to 10 carbon atoms, a substituted or unsubstituted aryl or cycloalkyl group, or a saturated or unsaturated cyclic group having a heteroatom which is N, O, or S in the ring; and $R^2$ and $R^3$ independently represent hydrogen or a substituted or unsubstituted normal or branched alkyl group having 1 to 10 carbon atoms, or $R^1$ and $R^2$, or $R^2$ and $R^3$, and the nitrogen atom are members of a heterocyclic group having three to seven carbon atoms, the individual carbon atoms of the heterocyclic group independently being substituted or unsubstituted. Substituents on the $R^1$, $R^2$, and $R^3$ groups, or a heterocyclic group of which they are included, independently include, without limitation thereto, alkyl groups having 1 to about 6 carbon atoms, halogen, and the like, or either —OR or —OCOR, where R is hydrogen, alkyl having 1 to 10 carbon atoms, aryl, arylalkyl, or heteroaromatic.

The amino acid amides are prepared by reacting an amino acid having the structure:

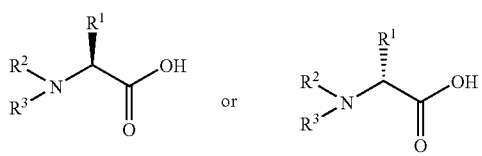

wherein $R^1$, $R^2$, and $R^3$ are as described above, or an acid salt of the amino acid, with a halogenating agent such as thionyl chloride, phosphorus pentachloride, or oxalyl chloride, or by forming a leaving group on the carboxylic acid function of the amino acid such as by forming an anhydride or ester derivative by known methods, to form an intermediate, then reacting the intermediate with ammonia.

Amine hydrochlorides or other acid salts can also be used as starting materials for the reaction. Starting with the amino acid salt (S)-2-aminobutyric acid hydrochloride, the reactions can prepare (S)-2-aminobutyramide hydrochloride, an intermediate in the process discussed below for preparing levetiracetam.

The intermediate that forms from the reaction of the amino acid or amino acid salt with the halogenating agent or leaving group precursor does not always have to be isolated before commencing the subsequent reaction with ammonia, providing a processing advantage.

In another aspect, the invention includes a process for preparing levetiracetam, comprising reacting (S)-2-aminobutyramide hydrochloride with a compound having the structure:

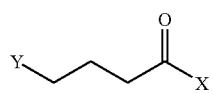

where X is a carboxylic acid activating group, and Y is Cl, Br, I, mesyl, tosyl, and the like. This process is exemplified by the scheme depicted in FIG. 1, where levetiracetam is formed from the reaction between (S)-2-aminobutyramide hydrochloride and 4-chlorobutyryl chloride. In this scheme, the isolation of 2-Aminobutyric acid methyl ester hydrochloride is optional, prior to its further reaction with ammonia.

The term "carboxylic acid activating group" includes, in addition to the halides Cl, Br, and I, a mixed anhydride formed by reaction with reagents such as ethyl chloroformate, isobutylchloroformate, etc., an activated ester such as is formed by reaction with p-nitrophenol, pentafluorophenol, etc., or an adduct with a carbodiimide derivative such as dicyclohexylcarbodiimide, etc. This carboxylic acid activation is the same as is commonly used for peptide bond formation.

The invention is further illustrated by the following examples, which show only certain aspects and are not to be construed as limiting the invention defined by the appended claims.

EXAMPLE 1

The compound (S)-2-aminobutyramide hydrochloride is prepared by dissolving 50 grams of (S)-2-aminobutyric acid hydrochloride in 100 mL of methanol, and adding 28.7 mL of thionyl chloride while maintaining the reaction mixture temperature below about 55° C., then stirring until the reaction is complete. A vacuum is applied and maintained until the methanol has been distilled from the mixture. Isopropanol is then added, followed by the introduction of ammonia gas at a pressure about 60 psi (413 kPa) until the reaction is complete. After filtering to remove formed ammonium chloride, the solvent is partially evaporated and isopropanol hydrochloride is added. The mixture is stirred while solid product forms, then the solid is separated by filtration and washed with isopropanol.

The product was characterized by the following $^1$H NMR data (200 MHz, DMSO-$d_6$): 0.9-1.0(t,3H), 1.8-1.9(Q,2H), 3.7-3.8(t, 1H), 7.5-7.7(Br,$NH_2$), 8.0-8.2(Br,$NH_2$)

EXAMPLE 2

L-threonine amide hydrochloride is prepared by the dropwise addition of 1.5 equivalents of thionyl chloride to a solution of 50 grams L-threonine in methanol, then heating the mixture to reflux. When reaction is complete, as shown by periodic TLC analysis, the reaction mixture is cooled and concentrated under vacuum. Isopropanol is added and the solvent is evaporated under vacuum to remove residual thionyl chloride, then additional isopropanol is added to increase the volume about two to four times.

The reaction mixture is placed into an autoclave and stirred as ammonia gas is introduced to a final pressure of 50-60 psi (345-415 kPa), and stirring continues as the reaction progresses. After completion of the reaction, as shown by TLC analysis, the mixture is removed from the autoclave and filtered to remove solids, then concentrated under vacuum to about 100 mL. About 1.5 equivalents of isopropanol hydrochloride are added dropwise at room temperature, then the solid product is separated by filtration, washed with isopropanol and dried.

The product is characterized by the following $^1$H NMR data (200 MHz, DMSO-$d_6$): 1.1-1.2(d,3H), 3.3-3.4(s.OH), 3.5-3.6(d,1H), 3.9-4.1(sextet,1H), 5.5-5.7(d,$NH_2$), 7.6-7.8 (s,1 NH), 8.0-8.1(s,1 NH).

EXAMPLE 3

Using the general procedure of preceding Example 2, L-prolinamide hydrochloride is prepared, starting with L-proline. The product is characterized by the following $^1$H NMR data (200 MHz, DMSO-$d_6$): 1.9-2.0(quintet,2H), 2.1-2.3 (pentet,2H), 3.1-3.3(t,2H), 4.1-4.2(dd,1H), 7.6-7.8(Br,NH), 8.0-8.1(Br,NH), 8.9-9.8(Br,$NH_2$).

EXAMPLE 4

Using the general procedure of preceding Example 2, L-4-hydroxy-prolinamide hydrochloride is prepared, starting with L-4-hydroxyproline. The product is characterized by the following $^1$H NMR data (200 MHz, DMSO-$d_6$): 2.1-2.2(dd, 2H), 2.6-2.7(d,2H), 3.5-3.7(t,1H), 4.2-4.4(m,1H), 5.7-5.8(s, OH), 7.6-7.7(s,NH), 8.1-8.2(s,NH), 9.1-9.6(Br,NH).

EXAMPLE 5

The compound (−)-(S)-α-ethyl-2-oxo-1-pyrrolidineacetamide is prepared by suspending 50 grams of (S)-2-aminobutyramide hydrochloride in 500 mL of dichloromethane at room temperature, then cooling to temperatures between −5 and 0° C. and adding 81.2 grams of potassium hydroxide and 23.3 grams of tetrabutylammonium bromide at those temperatures. A 66.4 gram amount of 4-chlorobutyryl chloride is added at the same temperatures. After completion of the reaction, solids are removed by filtration, the solution is adjusted to pH 7-7.5 with acetic acid, and dichloromethane is partially evaporated by the application of a vacuum. 150 mL of ethyl acetate are added to precipitate the product, which is isolated by filtration and washed with ethyl acetate and then with acetone; the product has a chiral purity of 99.8 percent by high performance liquid chromatography. The final product is purified by recrystallization from ethyl acetate, giving a yield of 60-65 percent.

What is claimed is:

1. A process for preparing (−)-(S)-α-ethyl-2-oxo-1-pyrrolidineacetamide, comprising reacting (S)-2-aminobutyramide hydrochloride with a compound having the structure:

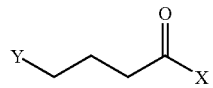

wherein X is a carboxylic activating group and Y is Cl, Br, I, mesyl, or tosyl in the presence of tetrabutylammonium bromide; adjusting pH to from about 7 to about 7.5; and recovering (−)-(S)-α-ethyl-2-oxo-1-pyrrolidineacetamide.

2. The process of claim 1, wherein the carboxylic activating group is Cl, Br, or I.

3. A process for preparing (−)-(S)-α-ethyl-2-oxo-1-pyrrolidineacetamide, comprising reacting (S)-2-aminobutyric acid hydrochloride with thionyl chloride to form an intermediate, reacting the intermediate with ammonia to form (S)-2-aminobutyramide hydrochloride, and reacting the (S)-2-aminobutyramide hydrochloride with 4-chlorobutyryl chloride in the presence of potassium hydroxide and tetrabutylammonium bromide.

4. The process of claim 1, wherein reacting occurs in the presence of potassium hydroxide and tetrabutylammonium bromide.

5. The process of claim 1, comprising reacting (S)-2-aminobutyramide hydrochloride with 4-chlorobutyryl chloride.

* * * * *